US007662792B2

(12) United States Patent
Phillips et al.

(10) Patent No.: US 7,662,792 B2
(45) Date of Patent: Feb. 16, 2010

(54) MODULATION OF FAS AND FASL EXPRESSION

(75) Inventors: Nigel C. Phillips, Pointe-Claire (CA); Mario C. Filion, Laval (CA)

(73) Assignee: Bioniche Life Sciences Inc., Belleville, Ontario (CA)

( * ) Notice: Subject to any disclaimer, the term of this patent is extended or adjusted under 35 U.S.C. 154(b) by 512 days.

(21) Appl. No.: 10/280,274

(22) Filed: Oct. 25, 2002

(65) Prior Publication Data

US 2003/0119776 A1 Jun. 26, 2003

Related U.S. Application Data

(60) Division of application No. 09/879,668, filed on Jun. 12, 2001, now abandoned, and a continuation of application No. 09/735,363, filed on Dec. 12, 2000.

(60) Provisional application No. 60/228,925, filed on Aug. 29, 2000, provisional application No. 60/266,229, filed on Feb. 2, 2001, provisional application No. 60/170,325, filed on Dec. 13, 1999.

(51) Int. Cl.
*A61K 31/70* (2006.01)
(52) U.S. Cl. ...................................... 514/44
(58) Field of Classification Search .................. 514/44
See application file for complete search history.

(56) References Cited

U.S. PATENT DOCUMENTS

| 4,791,101 | A | * | 12/1988 | Adolf | 424/85.1 |
| 4,983,518 | A | | 1/1991 | Schaffner et al. | |
| 5,643,890 | A | * | 7/1997 | Iversen et al. | 514/44 |
| 6,015,710 | A | * | 1/2000 | Shay et al. | 435/375 |
| 6,150,339 | A | * | 11/2000 | Rando et al. | 514/44 |
| 6,316,190 | B1 | * | 11/2001 | Rein et al. | 435/6 |
| 7,125,858 | B2 | * | 10/2006 | Filion et al. | 514/44 |

FOREIGN PATENT DOCUMENTS

| WO | WO 94/08053 A | | 4/1994 |
| WO | WO 9417086 A1 | * | 8/1994 |
| WO | WO 96/23508 A | | 8/1996 |
| WO | WO 97/20924 A | | 6/1997 |

OTHER PUBLICATIONS

Ohyashiki, K. et al. Leukemia (1997) vol. 11, pp. 190-194.*
Liu, X. et al. Expert Opinion on Therapeutic Patents (1996) vol. 6, pp. 457-470.*
Coussens et al. (Nature 2002. vol. 420, pp. 860-867).*
Griffith, et al., "Fas Ligand-Induced Apoptosis as a Mechanism of Immune Privilege," Science, Nov. 17, 1995, pp. 1189-1192, vol. 270.
Morassutti, et al., "Correlation between cytotoxic effect and binding to nuclear proteins of oligomeric d(GT)n sequences in human cancer CCRF-CEM cell line," Minerva Biotec, Jun. 1995, pp. 176-181.
Filion, et al., "Modulation of interleukin-12 synthesis by DNA lacking the CpG motif and present in a mycobacterial cell wall complex," Cancer Immunol Immunother (Mar. 2000) 49:325-334.
Morassutti, et al., "Effect of Oligomer Length and Base Substitutions On The Cytotoxic Activity and Specific Nucelar Protein Recognition of GTn Oligonucleotides in the Human Leukemic CCRF-CEM Cell Line," Nucleosides and Nucleotides, 18(6&7), pp. 1711-1716(1999).
Reader, S., et al., "Identification of non-antisense phosphodiester oligonucleotides that induce cell cycle arrest and apoptosis in cancer cells," Clinical Cancer Research (Nov. 2000), vol. 6, Supp., pp. 4571S.
Ballas et al., "Induction of NK Activity in Murine and Human Cells by CpG Motifs in Oligodeoxynucleotides and Bacterial DNA," J. Immunol. Sep. 1, 1996, p. 1840-1845, vol. 157.
Bates et al., "Antiproliferative Activity of G-rich Oligonucleotides Correlates with Protein Binding," J. Biol. Chem., Sep. 10, 1999, p. 26369-26377, vol. 274.
Braun et al., "Cytotoxic T Cells Deficient in Both Functional Fas Ligand and Perforin Show Residual Cytolytic Activity yet Lose Their Capacity to Induce Lethal Acute Graft-Versus-Host Disease," J. Exp. Med., 1996, p. 657-661, vol. 183.
Famularo et al., "Fas/Fas Ligand on the Road; An Apoptotic Pathway Common to AIDS, Autoimmunity, Lymphoproliferation and Transplantation," Med. Hypoth., 1999, p. 50-62, vol. 53.
Hochhauser, D., Anti-Cancer Chemotherapeutic Agents, 1997, p. 903, vol. 8.
Klinman et al., "CpG Motifs Present in Bacterial DNA Rapidly Induce Lymphocytes to Secrete Interleukin 6, Interleukin 12, and Interferon y," Proc. Natl. Acad. Sci. USA, Apr. 1996, p. 2879-2883, vol. 93.
Kondo et al., "Essential Roles of the Fas Ligand in the Development of Hepatitis," Nature Med., Apr. 1997, p. 409-413. vol. 3, No. 4.
Lipford et al., "CpG-Containing Synthetic Oligonucleotides Promote B and Cytotoxic T Cell Responses to Protein Antigen: A New Class of Vaccine Adjuvants," Eur. J. Immunol., 1997, p. 2340-2344, vol. 27.
Nagata, S., "Fas Ligand-Induced Apoptosis," Ann. Rev. Genet., 1999, p. 29-55, vol. 33.
Nishioka et al., "An Augmentation of Fas (CD95/AP0-1) Antigen Induced by Radiation: Flow Cytometry Analysis of Lymphoma and Leukemia Cell Lines," Int. J. Mol. Med., 1999, p. 275-278, vol. 3.

(Continued)

*Primary Examiner*—J. E. Angell
(74) *Attorney, Agent, or Firm*—Kilpatrick Stockton LLP

(57) ABSTRACT

A method employing a composition comprising a 2 to 10 base synthetic oligonucleotide sequence selected from the group consisting of $(GG)_n$, $(GT)_n$, $a(GT)_nb$, $a(GA)_nb$, and $a(GC)_nb$, wherein n is an integer between 1 and 3, and a and b are independently either none or one or more As, Cs, Gs, or Ts, or combinations thereof, for modulation of Fas and FasL expression or for modulation of the efficacy of therapeutic agents. The composition is administered to an animal or human with a pharmaceutically acceptable carrier, and optionally with a therapeutic agent, in an amount effective to modulate Fas and FasL expression, to treat the disease, or to modulate efficacy of the therapeutic agent.

29 Claims, No Drawings

OTHER PUBLICATIONS

O'Connell, et al., "The Fas Counterattack: Fas-Mediated T Cell Killing by Colon Cancer Cells Expressing Fas Ligand," J. Exp. Med., Sep. 1996, p. 1075-1082, vol. 184.

Owen-Schaub et al., "Fas and Fas Ligand Interactions in Malignant Disease (Review)," Int. J. Oncol., 2000, p. 5-12, vol. 17.

Sabelko-Downes et al., "The Role of Fas Ligand in vivo as a Cause and Regulator of Pathogenesis," Curr. Opin. Immunol., Jun. 2000, p. 330-335, vol. 12.

Scaggiante et al., "Human Cancer Cell Lines Growth Inhibition by $GT_n$ Oligodeoxyribonucleotides Recognizing Single-Stranded DNA-Binding Proteins," Eur. J. Biochem., Mar. 1, 1998, p. 207-215, vol. 252.

Sheard et al., "Up-Regulation of Fas (CD95) in Human p534$^{wud-type}$ Cancer Cells Treated With Ionizing Radiation," Int. J. Cancer, Nov. 27, 1997, p. 757-762, vol. 73.

Vlassov et al., "Transport of Oligonucleotides across Natural and Model Membranes," Biochim. Biophys. Acta., 1994, p. 95-108, vol. 1197.

Wagner, R., "Gene Inhibition Using Antisense Oligodeoxynucleotides," Nature, 1994, p. 333-335, vol. 372.

Wang et al., "Unmethylated CpG Motifs Protect Murine B Lymphocytes Against Fas-Mediated Apoptosis," Cell Immunol., 1997, p. 162-167, vol. 180.

Wyllie et al., "Cell Death: The Significance of Apoptosis," Int. Rev. Cytol., 1980, p. 251-306, vol. 68.

Wyllie A., "Glucocorticoid-Induced Thymocyte Apoptosis is Associated with Endogenous Endonuclease Activation," Nature, 1980, p. 555-556, vol. 284.

Yoong et al., "Fas/Fas Ligand Interaction in Human Colorectal Hepatic Metastases," Am. J. Pathol., Mar. 1999, p. 693-703, vol. 154.

Filion, M.C. et al., "Inhibition of cell cycle progression and induction of apoptosis in leukemia cells by *Mycobacterium phlei* DNA and derived synthetic oligonucleotides." Clinical Cancer Research (Nov. 7-10, 2000), vol. 6, Supp.; p. 4571S.

Filion, M.C., et al., "*Mycobacterium phlei* cell wall complex directly induces apoptosis in human bladder cancer cells." British Journal of Cancer (Jan., 1999) 79(2) 229-35.

Promega Catalog 1993/94, Revolutions in Science, cover and pp. 90-91.

* cited by examiner

SEQUENCE LISTING

```
<160> NUMBER OF SEQ ID NOS: 18

<210> SEQ ID NO 1
<211> LENGTH: 6
<212> TYPE: DNA
<213> ORGANISM: Artificial Sequence
<220> FEATURE:
<223> OTHER INFORMATION: Synthetic phosphodiester oligodeoxynucleotide

<400> SEQUENCE: 1 tgtgtg                                                                  6

<210> SEQ ID NO 2
<211> LENGTH: 6
<212> TYPE: DNA
<213> ORGANISM: Artificial Sequence
<220> FEATURE:
<223> OTHER INFORMATION: Synthetic phosphodiester oligodeoxynucleotide

<400> SEQUENCE: 2 gtgtgt                                                                  6

<210> SEQ ID NO 3
<211> LENGTH: 6
<212> TYPE: DNA
<213> ORGANISM: Artificial Sequence
<220> FEATURE:
<223> OTHER INFORMATION: Synthetic phosphodiester oligodeoxynucleotide
```

```
<400> SEQUENCE: 3 tttgtt                                                                 6

<210> SEQ ID NO 4
<211> LENGTH: 6
<212> TYPE: DNA
<213> ORGANISM: Artificial Sequence
<220> FEATURE:
<223> OTHER INFORMATION: Synthetic phosphodiester oligodeoxynucleotide

<400> SEQUENCE: 4 ggtggg                                                                 6

<210> SEQ ID NO 5
<211> LENGTH: 6
<212> TYPE: DNA
<213> ORGANISM: Artificial Sequence
<220> FEATURE:
<223> OTHER INFORMATION: Synthetic phosphodiester oligodeoxynucleotide

<400> SEQUENCE: 5 gggtgg                                                                 6

<210> SEQ ID NO 6
<211> LENGTH: 6
<212> TYPE: DNA
<213> ORGANISM: Artificial Sequence
<220> FEATURE:
<223> OTHER INFORMATION: Synthetic phosphodiester oligodeoxynucleotide

<400> SEQUENCE: 6 ttgttt                                                                 6

<210> SEQ ID NO 7
<211> LENGTH: 6
<212> TYPE: DNA
<213> ORGANISM: Artificial Sequence
<220> FEATURE:
<223> OTHER INFORMATION: Synthetic phosphodiester oligodeoxynucleotide

<400> SEQUENCE: 7 aagtaa                                                                 6

<210> SEQ ID NO 8
<211> LENGTH: 6
<212> TYPE: DNA
<213> ORGANISM: Artificial Sequence
<220> FEATURE:
<223> OTHER INFORMATION: Synthetic phosphodiester oligodeoxynucleotide

<400> SEQUENCE: 8 ccgtcc                                                                 6

<210> SEQ ID NO 9
<211> LENGTH: 6
<212> TYPE: DNA
<213> ORGANISM: Artificial Sequence
<220> FEATURE:
<223> OTHER INFORMATION: Synthetic phosphodiester oligodeoxynucleotide

<400> SEQUENCE: 9 tggttg                                                                 6

<210> SEQ ID NO 10
<211> LENGTH: 6
```

```
<212> TYPE: DNA
<213> ORGANISM: Artificial Sequence
<220> FEATURE:
<223> OTHER INFORMATION: Synthetic phosphodiester oligodeoxynucleotide

<400> SEQUENCE: 10 atgtat                                                                      6

<210> SEQ ID NO 11
<211> LENGTH: 6
<212> TYPE: DNA
<213> ORGANISM: Artificial Sequence
<220> FEATURE:
<223> OTHER INFORMATION: Synthetic phosphodiester oligodeoxynucleotide

<400> SEQUENCE: 11 ctgtct                                                                      6

<210> SEQ ID NO 12
<211> LENGTH: 6
<212> TYPE: DNA
<213> ORGANISM: Artificial Sequence
<220> FEATURE:
<223> OTHER INFORMATION: Synthetic phosphodiester oligodeoxynucleotide

<400> SEQUENCE: 12 tcgttc                                                                      6

<210> SEQ ID NO 13
<211> LENGTH: 6
<212> TYPE: DNA
<213> ORGANISM: Artificial Sequence
<220> FEATURE:
<223> OTHER INFORMATION: Synthetic phosphodiester oligodeoxynucleotide

<400> SEQUENCE: 13 ggttgg                                                                      6

<210> SEQ ID NO 14
<211> LENGTH: 6
<212> TYPE: DNA
<213> ORGANISM: Artificial Sequence
<220> FEATURE:
<223> OTHER INFORMATION: Synthetic phosphodiester oligodeoxynucleotide

<400> SEQUENCE: 14 ggaagg                                                                      6

<210> SEQ ID NO 15
<211> LENGTH: 6
<212> TYPE: DNA
<213> ORGANISM: Artificial Sequence
<220> FEATURE:
<223> OTHER INFORMATION: Synthetic phosphodiester oligodeoxynucleotide

<400> SEQUENCE: 15 ggccgg                                                                      6

<210> SEQ ID NO 16
<211> LENGTH: 6
<212> TYPE: DNA
<213> ORGANISM: Artificial Sequence
<220> FEATURE:
<223> OTHER INFORMATION: Synthetic phosphodiester oligodeoxynucleotide

<400> SEQUENCE: 16
```

```
                                    -continued gggggg                                                                  6

<210> SEQ ID NO 17
<211> LENGTH: 6
<212> TYPE: DNA
<213> ORGANISM: Artificial Sequence
<220> FEATURE:
<223> OTHER INFORMATION: Synthetic phosphodiester oligodeoxynucleotide

<400> SEQUENCE: 17 gggagg                                                                  6

<210> SEQ ID NO 18
<211> LENGTH: 6
<212> TYPE: DNA
<213> ORGANISM: Artificial Sequence
<220> FEATURE:
<223> OTHER INFORMATION: Synthetic phosphodiester oligodeoxynucleotide

<400> SEQUENCE: 18 gggcgg                                                                  6
```

MODULATION OF FAS AND FASL EXPRESSION

PRIOR RELATED APPLICATIONS

This application claims priority to PCT patent application serial number PCT/CA00/01467 filed Dec. 12, 2000, which claims priority to U.S. provisional patent applications Ser. Nos. 60/228,925 filed Aug. 29, 2000 and 60/170,325 filed Dec. 13, 1999. The present patent application also claims priority to U.S. provisional patent applications Ser. Nos. 60/228,925 filed Aug. 29, 2000, and 60/266,229 filed Feb. 2, 2001, and to U.S. non-provisional patent application Ser. No. 09/735,363 filed Dec. 12, 2000. The present patent application is a divisional of U.S. patent application Ser. No. 09/879,668 filed Jun. 12, 2001 now abandoned.

FIELD OF THE INVENTION

The present invention relates compositions useful for modulating Fas and Fas ligand expression on cells and for modulating efficacy of therapeutic agents.

BACKGROUND OF THE INVENTION

The Fas (Apo-1, CD95) and Fas ligand (FasL, CD95L) system is one of the best-studied cell death systems. Fas is a type-I membrane protein abundantly expressed by cells in various tissues and particularly on activated T cells, heart cells, kidney cells and hepatocytes. FasL is a type-II transmembrane protein expressed particularly on activated T cells and natural killer cells (Nagata, S. Ann. Rev. Genet. 33:29, 1999), and is expressed constitutively in immune-privileged sites as, for example, the eye and testis (Griffith et al. Science 270:630, 1995).

Fas and FasL interactions (Fas/FasL) play an essential role in the regulation of immune cells and in the elimination of autoreactive cells (Sabelko-Downes et al. Curr. Opin. Immunol. 12:330, 2000). In addition, Fas/FasL mediates the killing of cancer cells and of virus-infected cells (Famularo et al. Med. Hypoth. 53:50, 1999; Owen-Schaub et al. Int. J. Oncol. 17:5, 2000). In contrast, FasL, expressed on cancer cells, may attack cells of the immune system (O'Connell, J. Exp. Med. 184:1075, 1996) or facilitate local tumor invasion by killing surrounding tissue (Yoong et al. Am. J. Pathol. 154:693, 1999). FasL, expressed on activated T cells, may also participate in tissue damage in fulminant hepatitis and in graft-versus-host disease (Kondo et al. Nature Med. 3:409, 1997; Braun et al. J. Exp. Med. 183:657, 1996).

Binding of FasL to Fas, or cross-linking of Fas with agonistic antibodies, induces apoptosis (Nagata, S. Ann. Rev. Genet. 33:29, 1999) that results in cell death. Apoptosis is an active cellular death process characterized by distinctive morphological changes that include condensation of nuclear chromatin, cell shrinkage, nuclear disintegration, plasma membrane blebbing, and the formation of membrane-bound apoptotic bodies (Wyllie et al. Int. Rev. Cytol. 68:251, 1980). A molecular hallmark of apoptosis is degradation of cellular nuclear DNA into oligonucleosomal-length fragments as the result of activation of endogenous endonucleases (Wyllie A. Nature 284:555, 1980). Caspases (cysteine-aspartyl-specific proteases) have been implicated as key enzymes in the execution of the late stage of apoptosis. The binding of FasL to Fas activates a cascade of caspases via a FADD adaptor (Fas-associated protein with death domain), which leads to the cleavage of various cellular substrates and to DNA fragmentation (Nagata, S. Ann. Rev. Genet. 33:29, 1999).

Synthetic oligonucleotides are polyanionic sequences that can be internalized by cells (Vlassov et al. Biochim. Biophys. Acta 1197:95, 1994) and bind selectively to nucleic acids (Wagner, R. Nature: 372:333, 1994), to specific cellular proteins (Bates et al. J. Biol. Chem. 274:26369, 1999) and to specific nuclear proteins (Scaggiante et al. Eur. J. Biochem. 252:207, 1998), and inhibit cell proliferation. Proliferation is the culmination of the progression of a cell through the cell cycle, resulting in the division of one cell into two cells. Alterations in cell cycle progression occur in all cancers and may result from over-expression of genes, mutation of regulatory genes, or abrogation of DNA damage checkpoints (Hochhauser D. Anti-Cancer Chemotherapeutic Agents 8:903, 1997).

Synthetic phosphorothioate oligonucleotides containing unmethylated CpG dinucleotides flanked by two 5' purine and two 3' pyrimidine (CpG motifs) are reported to induce the synthesis of cytokines by macrophages and B cells, to increase the activity of NK cells and cytotoxic T lymphocytes, and to enhance T-helper 1 response (Ballas et al. J. Immunol. 157:1840, 1996; Klinman et al. Proc. Natl. Acad. Sci. U.S.A. 93:2879, 1996; Lipford et al. Eur. J. Immunol. 27:2340, 1997). A 20 base synthetic CpG motif is reported to block Fas expression on activated B cells and to block apoptosis induced by anti-Fas monoclonal antibodies (Wang et al. Cell. Immunol. 180:162, 1997). Irradiation is reported to upregulate the expression of Fas on cancer cells (Sheard et al. Int. J. Cancer 73:757, 1997; Nishioka et al. Int. J. Mol. Med. 3:275, 1999).

The ability to modulate the Fas/FasL system has many clinical applications for use in diseases including, but not limited to, neoplastic autoimmune, degenerative and cardiovascular diseases. However, most prior Fas/FasL modulating agents have proven to be less than adequate in clinical applications. Moreover, many of these agents are inefficient, toxic or have significant adverse effects.

Therefore, there is a continuing need for novel compositions and methods that modulate the expression of Fas and FasL on cells. There is also a need for novel compositions and methods that modulate the efficacy of Fas and FasL modulatory agents on disease. There is also a need for novel compositions and methods that modulate the expression of Fas and FasL on cells in order to treat diseases in animals or humans associated with altered expression of Fas or FasL on cells.

SUMMARY OF THE INVENTION

The present invention fulfills these needs by providing a novel method, employing new compositions comprising a synthetic phosphodiester oligodeoxynucleotide (hereinafter, "sequence") selected from the group consisting of $(GG)_n$, $(GT)_n$, $a(GT)_nb$, $a(GA)_nb$, and $a(GC)_nb$, wherein n is an integer between 1 and 3, and a and b are independently either none or one or more As, Cs, Gs, or Ts, or combinations thereof, wherein the total number of bases in the composition is between 2 and 10, preferably 4 to 8, more preferably 5 to 7, and most preferably 6.

The present invention provides new uses for these compositions. This composition is combined with a pharmaceutically acceptable carrier, and is administered to an animal or a human in an amount effective to modulate Fas and FasL expression in the animal or the human. This composition is also combined with a pharmaceutically acceptable carrier, and is administered to an animal or a human having a disease in an amount effective to modulate Fas and FasL expression in order to treat the disease in the animal or the human. This composition is also administered to an animal or human to modulate the efficacy of Fas and FasL modulatory agents, comprising administration of the composition in an amount effective to modulate efficacy of Fas and FasL modulatory agents to modulate Fas and FasL, or to treat an animal or a human having a disease. Another new use for this composition of the present invention is to modulate, and preferentially potentiate, the efficacy of a therapeutic agent to treat a disease, comprising administration of the composition in a pharmaceutically acceptable carrier, optionally in combination with a therapeutic agent, in an amount effective to modulate efficacy of the therapeutic agent administered to an animal or a human. The compositions of the present invention may be administered at any time before, during, or after administration of the therapeutic agent, in order to modulate the efficacy of the therapeutic agent. The compositions of the present invention may also be administered in vitro, for example to animal or human cells or tissues.

In a preferred embodiment, the composition of the present invention comprises a sequence selected from the group consisting of $(GG)_n$, $(GT)_n$, $a(GT)_nb$, $a(GA)_nb$, and $a(GC)_nb$, wherein n is an integer between 1 and 3, and a and b are independently either none or one or more As, Cs, Gs, or Ts, or combinations thereof provided the total number of bases in the composition is 6. In another preferred embodiment, the composition of the present invention comprises this sequence of 6 bases in combination with a pharmaceutically acceptable carrier. In yet another preferred embodiment, the composition of the present invention comprises this sequence of 6 bases in combination with a therapeutic agent and a pharmaceutically acceptable carrier. These compositions may be used in any of the methods described in the preceding paragraphs and throughout the specification.

The unexpected and surprising ability of the sequences of the present invention to modulate the expression of Fas and FasL addresses a long felt unfulfilled need in the medical arts and provides an important benefit for animals, including humans.

Accordingly, an object of the present invention is to provide a new composition comprising a synthetic phosphodiester oligodeoxynucleotide (hereinafter, "sequence") selected from the group consisting of $(GG)_n$, $(GT)_n$, $a(GT)_nb$, $a(GA)_nb$, and $a(GC)_nb$, wherein n is an integer between 1 and 3, and a and b are independently either none or one or more As, Cs, Gs, or Ts, or combinations thereof, wherein the total number of bases in the composition is 2 to 10.

Another object of the present invention is to provide a new composition comprising a synthetic phosphodiester oligodeoxynucleotide (hereinafter, "sequence") selected from the group consisting of $(GG)_n$, $(GT)_n$, $a(GT)_nb$, $a(GA)_nb$, and $a(GC)_nb$, wherein n is an integer between 1 and 3, and a and b are independently either none or one or more As, Cs, Gs, or Ts, or combinations thereof, wherein the total number of bases in the composition is 4 to 8.

Yet another object of the present invention is to provide a new composition comprising a synthetic phosphodiester oligodeoxynucleotide (hereinafter, "sequence") selected from the group consisting of $(GG)_n$, $(GT)_n$, $a(GT)_nb$, $a(GA)_nb$, and $a(GC)_nb$, wherein n is an integer between 1 and 3, and a and b are independently either none or one or more As, Cs, Gs, or Ts, or combinations thereof, wherein the total number of bases in the composition is 5 to 7.

Another object of the present invention is to provide a new composition comprising a synthetic phosphodiester oligodeoxynucleotide (hereinafter, "sequence") selected from the group consisting of $(GG)_n$, $(GT)_n$, $a(GT)_nb$, $a(GA)_nb$, and $a(GC)_nb$, wherein n is an integer between 1 and 3, and a and b are independently either none or one or more As, Cs, Gs, or Ts, or combinations thereof, wherein the total number of bases in the composition is 6.

Yet another object of the present invention is to provide novel compositions comprising any of the sequences described herein, in combination with a pharmaceutically acceptable carrier.

Another object of the present invention is to provide novel compositions comprising any of the sequences described herein, in combination with a therapeutic agent and a pharmaceutically acceptable carrier.

Yet another object of the present invention is to provide for the use of any of the novel compositions described herein for the manufacture of a medicament.

Still another object of the present invention is to provide new uses for the compositions of the present invention.

Yet another object of the present invention is to provide a method to modulate the Fas expression on cells.

Another object of the present invention is to provide a method to modulate FasL expression on cells.

Still another object of the present invention is to provide a method to modulate the Fas expression on immune cells.

Another object of the present invention is to provide a method to modulate FasL expression on immune cells.

Yet another object of the present invention is to provide a method to modulate Fas expression on cancer cells.

Another object of the present invention is to provide a method to modulate FasL expression on cancer cells.

Another object of the present invention is to provide a method to treat a disease in an animal, including a human.

Yet another object of the present invention is to provide a method to treat a neoplastic disease.

Still another object of the present invention is to provide a method to treat an autoimmune disease.

Another object of the present invention is to provide a method to treat an inflammatory disease.

Yet another object of the present invention is to provide a method to treat a proliferative disease Another object of the present invention is to provide a method to treat a lymphoproliferative disease.

Yet another object of the present invention is to provide a method to treat a degenerative disease.

Still another object of the present invention is to provide a method to treat a neurodegenerative disease.

Another object of the present invention is to provide a method to treat a cardiovascular disease Yet another object of the present invention is to provide a method to treat a graft rejection.

Another object of the present invention is to provide a method effective to treat an infection.

Yet another object of the present invention is to provide a method that modulates the effect of a therapeutic agent to treat disease.

Yet another object of the present invention is to provide a method that potentiates the effect of a therapeutic agent to treat disease.

Still another object of the present invention is to provide a method that potentiates the effect of a Fas modulating agent.

Another object of the present invention is to provide a method that potentiates the effect of a FasL modulating agent.

Yet another object of the present invention is to provide a method that potentiates the effect of an anti-neoplastic agent.

Another object of the present invention is to provide a method that potentiates the effect of an immunostimulatory agent.

Still another object of the present invention is to provide a method that potentiates the effect of an immunosuppressive agent.

Another object of the present invention is to provide a method that potentiates the effect of an anti-inflammatory agent.

It is another object of the present invention to provide a composition that is simple to prepare.

Another object of the present invention is to provide a composition that is minimally toxic to the recipient.

These and other objects, features and advantages of the present invention will become apparent after a review of the following detailed description of the disclosed embodiment and the appended claims.

DETAILED DESCRIPTION

The present invention fulfills these needs by providing new compositions and new methods of using these compositions. The present compositions comprise a synthetic phosphodiester oligodeoxynucleotide (hereinafter, "sequence") selected from the group consisting of $(GG)_n$, $(GT)_n$, $a(GT)_nb$, $a(GA)_nb$, and $a(GC)_nb$, wherein n is an integer between 1 and 3, and a and b are independently either none or one or more As, Cs, Gs, or Ts, or combinations thereof, wherein the total number of bases in the composition is between 2 and 10, preferably 4 to 8, more preferably 5 to 7, and most preferably 6. The compositions of the present invention further comprise any of the sequences described herein in combination with a pharmaceutically acceptable carrier. The compositions of the present invention further comprise any of the sequences described herein in combination with a therapeutic agent and a pharmaceutically acceptable carrier.

The present invention provides new uses for these novel compositions. This composition is combined with a pharmaceutically acceptable carrier, and is administered to an animal or a human an amount effective to modulate Fas and FasL expression in the animal or the human. This composition is also combined with a pharmaceutically acceptable carrier, and is administered to an animal or a human having a disease in an amount effective to modulate Fas and FasL expression in order to treat the disease in the animal or the human. This composition is also administered to an animal or human to modulate the efficacy of Fas and FasL modulatory agents, comprising administration of the composition in an amount effective to modulate efficacy of Fas and FasL modulatory agents to modulate Fas and FasL, or to treat an animal or a human having a disease. Another new use for this composition of the present invention is to modulate, and preferentially potentiate, the efficacy of a therapeutic agent to treat a disease, comprising administration of the composition in a pharmaceutically acceptable carrier, optionally in combination with a therapeutic agent, in an amount effective to modulate efficacy of the therapeutic agent administered to an animal or a human. The composition of the present invention may be administered at any time before, during, or after administration of the therapeutic agent, in order to modulate the efficacy of the therapeutic agent.

In a preferred embodiment the composition of the present invention comprises a sequence selected from the group consisting of $(GG)_n$, $(GT)_n$, $a(GT)_nb$, $a(GA)_nb$, and $a(GC)_nb$, wherein n is an integer between 1 and 3, and a and b are independently either none or one or more As, Cs, Gs, or Ts, or combinations thereof provided the total number of bases in the composition is 6. In another preferred embodiment, the composition of the present invention comprises this sequence of 6 bases in combination with a pharmaceutically acceptable carrier. In yet another preferred embodiment, the composition of the present invention comprises this sequence of 6 bases in combination with a therapeutic agent and a pharmaceutically acceptable carrier. These compositions may be used in any of the methods described in this patent application.

As used herein the word "sequence" refers to a synthetic phosphodiester oligodeoxynucleotide comprised of adenine (A), cytosine (C), guanine (G) and thymine (T), with a total number of bases of 2 to 10, preferably 4 to 8, more preferably 5 to 7 and most preferably 6.

As used herein, the word "expression" refers to the cell surface concentration of Fas or of FasL.

As used herein, the words "response" refers to upregulation (increase) or downregulation (decrease) of Fas or of Fas L expression.

As used herein, the word "modulates" refers to changes in the expression of Fas or of FasL. Such changes include upregulation and downregulation of Fas or of FasL expression. The word modulate is also employed to describe the ability of the novel sequences of the present invention to modulate the efficacy of therapeutic agents, including Fas and FasL modulating agents, to treat disease or to modulate Fas or FasL expression.

As used herein, the phrases "therapeutically effective", "effective amount" and "amount effective to" refer to an amount of a sequence effective to modulate the expression of Fas or of FasL.

As used herein, the word "disease" refers to a condition wherein bodily health is impaired.

As used herein, the phrase "therapeutic agent" is any agent approved by a regulatory agency of a country or a state government or listed in the U.S. Pharmacopoeia or other generally recognized pharmacopoeia for use to treat a disease in an animal, including a human.

As used herein, the word "antineoplastic" refers to preventing the development, maturation, proliferation or spread of cancer cells As used herein, the word "potentiates" refers to a degree of synergism that is greater than additive.

As used herein, the word "synergism" refers to the coordinated action of two or more agents.

Administration of an effective amount of a sequence of the present invention to an animal, including a human, is a therapeutic treatment that prevents, treats or eliminates a disease including, but not limited to, neoplastic, autoimmune, proliferative, lymphoproliferative, degenerative, and cardiovascular disease; infection; inflammation; and, graft, tissue and cell rejection.

Compositions comprising one or more sequences and a pharmaceutically acceptable carrier are prepared by uniformly and intimately bringing into association the sequence and the pharmaceutically acceptable carrier. Compositions comprising one or more sequences, a therapeutic agent and a pharmaceutically acceptable carrier are prepared by uniformly and intimately bringing into association the sequence, the therapeutic agent and the pharmaceutically acceptable carrier. Pharmaceutically acceptable carriers include liquid carriers, solid carriers or both. Liquid carriers are aqueous carriers, non-aqueous carriers or both and include, but are not limited to, solutions, suspensions and emulsions. Emulsions include, but are not limited to, oil emulsions, water in oil emulsions, water-in-oil-in-water emulsions, site-specific emulsions, long-residence emulsions, sticky-emulsions, microemulsions and nanoemulsions. Solid carriers are biological carriers, chemical carriers or both and include, but are not limited to, viral vector systems, plasmids, particles, microparticles, nanoparticles, microspheres, nanospheres, bacterial cell walls, minipumps, and biodegradable or non-biodegradable natural or synthetic polymers that allow for sustained release of the sequences.

Preferred aqueous carriers include, but are not limited to, water, saline and pharmaceutically acceptable buffers. Preferred non-aqueous carriers include, but are not limited to, a mineral oil or a neutral oil including, but not limited to, a diglyceride, a triglyceride, a phospholipid, a lipid, an oil and mixtures thereof, wherein the oil contains an appropriate mix of polyunsaturated and saturated fatty acids. Optionally, stabilizing agents and excipients may be included regardless of the pharmaceutically acceptable carrier used to present the sequence to the cells.

The therapeutic effectiveness of a sequence may be increased by methods including, but not limited to, chemically modifying the base, sugar or phosphate backbone, chemically supplementing or biotechnologically amplifying the sequences using bacterial plasmids containing the appropriate sequences, complexing the sequences to biological or chemical carriers or coupling the sequences to tissue-type or cell-type directed ligands or antibodies.

The composition of the present invention further comprises a composition comprising a sequence and a therapeutic agent, wherein, when the sequence and the therapeutic agent are combined with a pharmaceutically acceptable carrier and administered to an animal or human having a disease. The sequence modulates and preferentially potentiates the effect of the therapeutic agent on the disease.

Therapeutic agents include, but not limited to, anti-neoplastic, anti-inflammatory, anti-autoimmune, anti-degenerative, Fas modulating and FasL modulating agents, or any combination thereof, and radiation therapy, or a combination of radiation therapy with therapeutic agents. These therapeutic agents include, but are not limited to, biologicals, drugs, chemotherapeutic drugs, immunostimulants, immunomodulators, immunotherapeutics, anti-virals, anti-infectives, antibiotics, cytokines, antigens, antibodies, nucleic acids, vaccines, aptabases, nucleic acids, antisense nucleic acids, telomerase inhibitors, caspase inhibitors, caspase inducers, stable triple helix forming agents and genetic, biologically engineered and chemically synthesized agents, and agents that target cell death molecules for activation or inactivation.

Chemotherapeutic drugs include, but are not limited to, DNA damaging, DNA-alkylating, DNA-cross-linking, anti-tumor antibiotic, topoisomerase inhibiting, purine inhibiting, pyrimidine inhibiting, microtubule stabilizing, microtubule destabilizing, anti-metabolic, hormone antagonist, protein kinase inhibiting, HMG-CoA inhibiting, metaloproteinase inhibiting, CDK inhibiting, cyclin inhibiting, angiogenesis inhibiting, differentiation enhancing and molecular biologically modified viral, bacterial and extotoxic agents.

Routes of administration include, but are not limited to, oral, topical, subcutaneous, transdermal, subdermal, intra-muscular, intra-peritoneal, intra-vesical, intra-articular, intra-prostatic, intra-arterial, intra-venous, intra-dermal, intra-cranial, intra-lesional, intra-tumoral, intra-ocular, intra-pulmonary, intra-spinal, placement within cavities of the body, nasal inhalation and impression into skin. It is to be understood that administration of the compositions of the present invention may occur in vivo, ex vivo or in vitro. For example, the compositions of the present invention may be administered to animal or human cells or tissues in vitro. Appropriate doses for in vitro administration are about 1 nM to 1 mM, preferably about 10 nM to 100 μM, and more preferably about 100 nM to 10 μM.

Depending on the route of administration, the volume per dose is preferably about 0.001 to 100 ml per dose, more preferably about 0.01 to 50 ml per dose and most preferably about 0.1 to 30 ml per dose. A sequence in a pharmaceutically acceptable carrier, or sequence plus therapeutic agent in a pharmaceutically acceptable carrier, can be administered in a single dose treatment, in multiple dose treatments or continuously infused on a schedule and over a period of time appropriate to the disease being treated, the condition of the recipient and the route of administration. Moreover, the therapeutic agent can be administered before, concurrently with, or after administration of the sequence.

Preferably, the amount of sequence administered per dose is from about 0.001 to 100 mg/kg, more preferably from about 0.01 to 10 mg/ml and most preferably from about 0.1 to 5 mg/kg. A sequence plus a chemotherapeutic agent is administered to an animal having a disease in an amount effective to modulate, and preferentially potentiate, the effect of the therapeutic agent. Preferably, the amount of therapeutic agent administered per dose is from about 0.001 to 1000 mg/m$^2$ or from about 0.01 to 1000 mg/kg, more preferably from about 0.01 to 500 mg/m$^2$ or about 0.01 to 500 mg/kg and most preferably from about 0.1 to 100 mg/m$^2$ or about 0.1 to 100 mg/kg. In one embodiment of a therapeutic agent, anti-Fas antibodies are employed and are administered in a dose of from about 0.003 to about 0.3 mg/kg, preferably 0.01 to about 0.1 mg/kg.

The particular sequence and the particular therapeutic agent administered, the amount per dose, the dose schedule and the route of administration should be decided by the practitioner using methods known to those skilled in the art and will depend on the type of disease, the severity of the disease, the location of the disease and other clinical factors such as the size, weight and physical condition of the recipient. In addition, in vitro assays may optionally be employed to help identify optimal ranges for sequence and for sequence plus therapeutic agent administration.

The following examples will serve to further illustrate the present invention without, at the same time, however, constituting any limitation thereof. On the contrary, it is to be clearly understood that resort may be had to various other embodiments, modifications, and equivalents thereof which, after reading the description herein, may suggest themselves to those skilled in the art without departing from the spirit of the invention.

EXAMPLE 1

Preparation of Sequences

Phosphodiester sequences were prepared by Sigma-Genosys (Woodlands, Tex.) using Abacus Segmented Synthesis Technology. Unless stated otherwise, the sequences were dispersed in autoclaved deionized water or in a pharmaceutically acceptable buffer such as, but not limited to, saline immediately prior to use.

EXAMPLE 2

Cells

All cell lines were obtained from the American Type Culture Collection (ATCC, Rockville, Md.) and were cultured in the medium recommended by the ATCC. Table 1 shows the cell lines, their origins and their properties.

TABLE 1

Cell lines

| CELL LINE | ORIGIN | PROPERTIES |
|---|---|---|
| JURKAT | Human T cell leukemia | Suspension tumor model Atypical multi-drug resistance associated with p190-MRP protein |
| UMUC-3 | Human bladder cancer | P-glycoprotein overexpression |
| T-24 | Human bladder cancer | p53 mutated |
| LNCaP | Human prostate cancer | Solid tumor model; metastatic TGF-beta 1 receptor-negative; androgen-dependent |
| OVCAR-3 | Human ovarian cancer | Solid tumor model; metastatic p53 mutated; p21/waf-1/Cip-1 deleted |
| SK-OV-3 | Human ovarian cancer | Solid tumor model; metastatic TGF-beta 1 receptor-negative; androgen-dependent |
| MCF-7 | Human breast cancer | Solid tumor model; non-metastatic Caspase 3-negative; estrogen-depend |

Peripheral blood mononuclear cells (hereinafter, "PBMCs") were isolated from human blood by Ficoll-Hypaque (Amersham Pharmacia Biotech, Baie d'Urfée, Québec, Canada) density gradient centrifugation.

Cancer cells and PBMCs were seeded in 6 well flat-bottom microplates and were maintained at 37° C. in a 5% $CO_2$ atmosphere. Unless stated otherwise, $2 \times 10^5$ cells/ml were incubated for 48 h with 0 μg/ml (control) or 100 μg/ml (5.5 μM) (treated) of the sequences.

EXAMPLE 3

Measurement of Fas and of FasL at the Cell Surface

Fas and FasL expression were measured by flow cytometry using anti-Fas FITC-conjugated monoclonal antibodies and anti-FasL PE-conjugated monoclonal antibodies in a FACS-calibur Flow Cytometer (Becton Dickinson, San Jose, Calif., USA) using the CELLQuest program (Becton Dickinson).

Results are expressed as percentage (%) increase in the expression of Fas and of FasL measured on treated cells compared to control cells.

EXAMPLE 4

Modulation of Fas and FasL on Jurkat Leukemia T Cells

Jurkat human leukemia T cells are an a typical multi-drug resistant human suspension tumor cell model. Jurkat T cells were incubated with the 6 base sequences shown in Table 2.

TABLE 2

Percentage increase of Fas and of FasL on Jurkat human leukemia T cells

| | % INCREASE | |
|---|---|---|
| SEQUENCE | Fas | FasL |
| TGTGTG SEQ ID NO:1-(6 bases) | 52 | 93 |
| GTGTGT SEQ ID NO:2-(6 bases) | 52 | 43 |
| TTTGTT SEQ ID NO:3-(6 bases) | 258 | 497 |
| GGTGGG SEQ ID NO:4-(6 bases) | 61 | 22 |
| GGGTGG SEQ ID NO:5-(6 bases) | 150 | 145 |
| TTGTTT SEQ ID NO:6-(6 bases) | 126 | 140 |
| AAGTAA SEQ ID NO:7-(6 bases) | −4 | −21 |
| CCGTCC SEQ ID NO:8-(6 bases) | 107 | 151 |
| TGGTTG SEQ ID NO:9-(6 bases) | 362 | 952 |
| ATGTAT SEQ ID NO:10-(6 bases) | 246 | 393 |
| CTGTCT SEQ ID NO:11-(6 bases) | 203 | 413 |
| TCGTTC SEQ ID NO:12-(6 bases) | 121 | 75 |
| GGTTGG SEQ ID NO:13-(6 bases) | 99 | 86 |
| GGAAGG SEQ ID NO:14-(6 bases) | 67 | 88 |
| GGCCGG SEQ ID NO:15-(6 bases) | 75 | 41 |
| GGGGGG SEQ ID NO:16-(6 bases) | 118 | 49 |
| GGGAGG SEQ ID NO:17-(6 bases) | 77 | 91 |
| GGGCGG SEQ ID NO:18-(6 bases) | 208 | 356 |

EXAMPLE 5

Modulation of Fas and of FasL on PBMCs

PBMCs were incubated with the 6 base sequences shown in Table 3.

TABLE 3

Percentage increase of Fas and of FasL on PBMCs

| | % INCREASE | |
|---|---|---|
| SEQUENCE | Fas | FasL |
| TGTGTG SEQ ID NO:1-(6 bases) | 126 | 260 |
| GTGTGT SEQ ID NO:2-(6 bases) | 94 | 99 |
| TTTGTT SEQ ID NO:3-(6 bases) | 1165 | 1528 |
| GGTGGG SEQ ID NO:4-(6 bases) | 57 | 59 |
| GGGTGG SEQ ID NO:5-(6 bases) | 3 | −20 |
| TTGTTT SEQ ID NO:6-(6 bases) | 338 | 441 |
| AAGTAA SEQ ID NO:7-(6 bases) | 13 | −26 |
| CCGTCC SEQ ID NO:28-(6 bases) | 1046 | 1147 |
| TGGTTG SEQ ID NO:9-(6 bases) | 1043 | 1322 |
| ATGTAT SEQ ID NO:10-(6 bases) | 377 | 457 |
| CTGTCT SEQ ID NO:11-(6 bases) | 310 | 476 |
| TCGTTC SEQ ID NO:12-(6 bases) | 597 | 847 |
| GGTTGG SEQ ID NO:13-(6 bases) | −3 | −32 |
| GGAAGG SEQ ID NO:14-(6 bases) | 112 | 162 |

TABLE 3-continued

Percentage increase of Fas and of FasL on PBMCs

| SEQUENCE | % INCREASE | |
|---|---|---|
| | Fas | FasL |
| GGCCGG SEQ ID NO:15-(6 bases) | 6 | −29 |
| GGGGGG SEQ ID NO:16-(6 bases) | 38 | 42 |
| GGGAGG SEQ ID NO:17-(6 bases) | 266 | 356 |
| GGGCGG SEQ ID NO:18-(6 bases) | 523 | 850 |

EXAMPLE 6

Modulation of Fas and of FasL on T-24 Bladder Cancer Cells

T-24 bladder cancer cells are a p53 mutated human cell line T-24 cells ($1.0 \times 10^5$ cells/ml) were incubated with the 6 base sequences shown in Table 4.

TABLE 4

Percentage increase of Fas and of FasL on T-24 bladder cancer cells

| SEQUENCE | % INCREASE | |
|---|---|---|
| | Fas | FasL |
| TGTGTG SEQ ID NO:1-(6 bases) | 84 | 213 |
| GTGTGT SEQ ID NO:2-(6 bases) | 93 | 77 |
| TTTGTT SEQ ID NO:3-(6 bases) | 279 | 549 |
| GGTGGG SEQ ID NO:4-(6 bases) | 106 | 29 |
| GGGTGG SEQ ID NO:5-(6 bases) | 80 | 13 |
| TTGTTT SEQ ID NO:6-(6 bases) | 116 | 152 |
| AAGTAA SEQ ID NO:7-(6 bases) | 16 | −10 |
| CCGTCC SEQ ID NO:8-(6 bases) | 282 | 459 |
| TGGTTG SEQ ID NO:9-(6 bases) | 180 | 397 |
| ATGTAT SEQ ID NO:10-(6 bases) | 90 | 150 |
| CTGTCT SEQ ID NO:11-(6 bases) | 107 | 165 |
| TCGTTC SEQ ID NO:12-(6 bases) | 105 | 74 |
| GGTTGG SEQ ID NO:13-(6 bases) | 75 | 25 |
| GGAAGG SEQ ID NO:14-(6 bases) | 46 | 14 |
| GGCCGG SEQ ID NO:15-(6 bases) | 56 | 18 |
| GGGGGG SEQ ID NO:16-(6 bases) | 35 | −14 |
| GGGAGG SEQ ID NO:17-(6 bases) | 124 | 75 |
| GGGCGG SEQ ID NO:18-(6 bases) | 139 | 205 |

EXAMPLE 7

Modulation of Fas and of FasL on UMUC-3 Bladder Cancer Cells

UMUC-3 bladder cancer cells are a P-glycoprotein overexpressing human cell line. UMUC-3 cells ($1.0 \times 10^5$ cells/ml) were incubated with the 6 base sequences shown in Table 5.

TABLE 5

Percentage increase of Fas and of FasL on UMUC-3 bladder cancer cells

| SEQUENCE | % INCREASE | |
|---|---|---|
| | Fas | FasL |
| TGTGTG SEQ ID NO:1-(6 bases) | 72 | 112 |
| GTGTGT SEQ ID NO:2-(6 bases) | 72 | 154 |
| TTTGTT SEQ ID NO:3-(6 bases) | 108 | 231 |
| GGTGGG SEQ ID NO:4-(6 bases) | 62 | 113 |
| GGGTGG SEQ ID NO:5-(6 bases) | 67 | 143 |
| TTGTTT SEQ ID NO:6-(6 bases) | 57 | 132 |
| AAGTAA SEQ ID NO:7-(6 bases) | 6 | −1 |
| CCGTCC SEQ ID NO:8-(6 bases) | 55 | 149 |
| TGGTTG SEQ ID NO:9-(6 bases) | 143 | 300 |
| ATGTAT SEQ ID NO:10-(6 bases) | 42 | 95 |
| CTGTCT SEQ ID NO:11-(6 bases) | 45 | 156 |
| TCGTTC SEQ ID NO:12-(6 bases) | 47 | 112 |
| GGTTGG SEQ ID NO:13-(6 bases) | 47 | 98 |
| GGAAGG SEQ ID NO:14-(6 bases) | 1 | 8 |
| GGCCGG SEQ ID NO:15-(6 bases) | 23 | 58 |
| GGGGGG SEQ ID NO:16-(6 bases) | −5 | 10 |
| GGGAGG SEQ ID NO:17-(6 bases) | 39 | 106 |
| GGGCGG SEQ ID NO:18-(6 bases) | 72 | 250 |

EXAMPLE 8

Modulation of Fas and of FasL on OVCAR-3 Ovarian Cancer Cells

OVCAR-3 ovarian cancer cells are a p53 mutated, p21/waf-1/Cip deleted, metastatic human solid tumor model. OVCAR-3 cells were incubated with the 6 base sequences shown in Table 6.

TABLE 6

Percentage increase of Fas and of FasL on OVCAR-3 ovarian cancer cells

| SEQUENCE | % INCREASE | |
|---|---|---|
| | Fas | FasL |
| TGTGTG SEQ ID NO:1-(6 bases) | 64 | 70 |
| GTGTGT SEQ ID NO:2-(6 bases) | 77 | 69 |
| TTTGTT SEQ ID NO:3-(6 bases) | 193 | 341 |
| GGTGGG SEQ ID NO:4-(6 bases) | 41 | 14 |
| GGGTGG SEQ ID NO:5-(6 bases) | 43 | 9 |
| TTGTTT SEQ ID NO:6-(6 bases) | 65 | 98 |
| AAGTAA SEQ ID NO:7-(6 bases) | 16 | −2 |

TABLE 6-continued

Percentage increase of Fas and of FasL on OVCAR-3 ovarian cancer cells

| SEQUENCE | % INCREASE | |
|---|---|---|
| | Fas | FasL |
| CCGTCC SEQ ID NO:8-(6 bases) | 83 | 95 |
| TGGTTG SEQ ID NO:9-(6 bases) | 221 | 270 |
| ATGTAT SEQ ID NO:10-(6 bases) | 93 | 114 |
| CTGTCT SEQ ID NO:11-(6 bases) | 52 | 93 |
| TCGTTC SEQ ID NO:12-(6 bases) | 126 | 224 |
| GGTTGG SEQ ID NO:13-(6 bases) | 22 | 10 |
| GGAAGG SEQ ID NO:14-(6 bases) | 15 | 1 |
| GGCCGG SEQ ID NO:15-(6 bases) | 19 | −2 |
| GGGGGG SEQ ID NO:16-(6 bases) | −1 | 7 |
| GGGAGG SEQ ID NO:17-(6 bases) | 49 | 59 |
| GGGCGG SEQ ID NO:18-(6 bases) | 65 | 142 |

EXAMPLE 9

Modulation of Fas and of FasL on SK-OV 3 Ovarian Cancer Cells

SK-OV-3 ovarian cancer cells are a p53 mutated, p21/waf-1/Cip deleted, $p15^{ink4B}$, $p16^{ink4}$ deleted metastatic human solid tumor model. SK-OV 3 cells ($1.0 \times 10^5$ cells/ml) were incubated with the 6 base sequences shown in Table 7.

TABLE 7

Percentage increase of Fas and FasL on SK-OV-3 ovarian cancer cells

| SEQUENCE | % INCREASE | |
|---|---|---|
| | Fas | FasL |
| TGTGTG SEQ ID NO:1-(6 bases) | 49 | 37 |
| GTGTGT SEQ ID NO:2-(6 bases) | 60 | 24 |
| TTTGTT SEQ ID NO:3-(6 bases) | 108 | 103 |
| GGTGGG SEQ ID NO:4-(6 bases) | −1 | −17 |
| GGGTGG SEQ ID NO:5-(6 bases) | 3 | −31 |
| TTGTTT SEQ ID NO:6-(6 bases) | 41 | 24 |
| AAGTAA SEQ ID NO:7-(6 bases) | −12 | −22 |
| CCGTCC SEQ ID NO:8-(6 bases) | 58 | 32 |
| TGGTTG SEQ ID NO:9-(6 bases) | 63 | 53 |
| ATGTAT SEQ ID NO:10-(6 bases) | 34 | 33 |
| CTGTCT SEQ ID NO:11-(6 bases) | 15 | 26 |
| TCGTTC SEQ ID NO:12-(6 bases) | 9 | −3 |
| GGTTGG SEQ ID NO:13-(6 bases) | 16 | −3 |

TABLE 7-continued

Percentage increase of Fas and FasL on SK-OV-3 ovarian cancer cells

| SEQUENCE | % INCREASE | |
|---|---|---|
| | Fas | FasL |
| GGAAGG SEQ ID NO:14-(6 bases) | −15 | −31 |
| GGCCGG SEQ ID NO:15-(6 bases) | 0 | −27 |
| GGGGGG SEQ ID NO:16-(6 bases) | −14 | −28 |
| GGGAGG SEQ ID NO:17-(6 bases) | −6 | −16 |
| GGGCGG SEQ ID NO:18-(6 bases) | 29 | 42 |

EXAMPLE 10

Modulation of Fas and of FasL on LNCaP Prostate Cancer Cells

LNCaP prostate cancer cells are a TGF-beta 1 receptor negative, androgen-independent, metastatic human solid tumor model. LNCaP cells were incubated with the 6 base sequences shown in Table 8.

TABLE 8

Percentage increase of Fas and FasL on LNCaP prostate cancer cells

| SEQUENCE | % INCREASE | |
|---|---|---|
| | Fas | FasL |
| TGTGTG SEQ ID NO:1-(6 bases) | 29 | 40 |
| GTGTGT SEQ ID NO:2-(6 bases) | 34 | 5 |
| TTTGTT SEQ ID NO:3-(6 bases) | 199 | 344 |
| GGTGGG SEQ ID NO:4-(6 bases) | 21 | 8 |
| GGGTGG SEQ ID NO:5-(6 bases) | 15 | −1 |
| TTGTTT SEQ ID NO:6-(6 bases) | 40 | 73 |
| AAGTAA SEQ ID NO:7-(6 bases) | 0 | −16 |
| CCGTCC SEQ ID NO:8-(6 bases) | 0 | 311 |
| TGGTTG SEQ ID NO:9-(6 bases) | 184 | 241 |
| ATGTAT SEQ ID NO:10-(6 bases) | 44 | 68 |
| CTGTCT SEQ ID NO:11-(6 bases) | 17 | 55 |
| TCGTTC SEQ ID NO:12-(6 bases) | 111 | 171 |
| GGTTGG SEQ ID NO:13-(6 bases) | 23 | −3 |
| GGAAGG SEQ ID NO:14-(6 bases) | 26 | −4 |
| GGCCGG SEQ ID NO:15-(6 bases) | 12 | −4 |
| GGGGGG SEQ ID NO:16-(6 bases) | 6 | 13 |
| GGGAGG SEQ ID NO:17-(6 bases) | 48 | 55 |
| GGGCGG SEQ ID NO:18-(6 bases) | 55 | 126 |

EXAMPLE 11

Modulation of Fas and of FasL on MCF-7 breast cancer cells

MCF-7 human breast cancer cells are a caspase-3 negative, estrogen-dependent human solid tumor model. MCF-7 cells ($1\times10^5$ cells/ml) were incubated with the 6 base sequences shown in Table 9.

TABLE 9

Percentage increase of Fas and of FasL on MCF-7 breast cancer cells

| SEQUENCE | % INCREASE | |
|---|---|---|
| | Fas | FasL |
| TGTGTG SEQ ID NO:1-(6 bases) | 122 | 121 |
| GTGTGT SEQ ID NO:2-(6 bases) | 155 | 135 |
| TTTGTT SEQ ID NO:3-(6 bases) | 361 | 528 |
| GGTGGG SEQ ID NO:4-(6 bases) | 106 | 110 |
| GGGTGG SEQ ID NO:5-(6 bases) | 93 | 81 |
| TTGTTT SEQ ID NO:6-(6 bases) | 143 | 159 |
| AAGTAA SEQ ID NO:7-(6 bases) | 12 | 21 |
| CCGTCC SEQ ID NO:8-(6 bases) | 200 | 322 |
| TGGTTG SEQ ID NO:9-(6 bases) | 255 | 481 |
| ATGTAT SEQ ID NO:10-(6 bases) | 129 | 214 |
| CTGTCT SEQ ID NO:11-(6 bases) | 73 | 128 |
| TCGTTC SEQ ID NO:12-(6 bases) | 56 | 98 |
| GGTTGG SEQ ID NO:13-(6 bases) | 99 | 83 |
| GGAAGG SEQ ID NO:14-(6 bases) | 62 | 84 |
| GGCCGG SEQ ID NO:15-(6 bases) | 63 | 78 |
| GGGGGG SEQ ID NO:16-(6 bases) | -7 | 18 |
| GGGAGG SEQ ID NO:17-(6 bases) | 127 | 194 |
| GGGCGG SEQ ID NO:18-(6 bases) | 165 | 322 |

EXAMPLE 12

Inhibition of Fas expression on Jurkat Human Leukemia T Cells by Cycloheximide

Jurkat human leukemia T cells were pre-incubated with 0.0 μg/ml (−CHX) or with 0.1 μg/ml of cycloheximide (+CHX) for 1 h. Ten μg/ml or 100 μg/ml of 6 base SEQ ID NO:5 (GGGTGG) was added to both the −CHX and +CHX cells and the incubation was continued for 24 hours and for 48 hours (Table 10).

TABLE 10

Percentage increase of Fas on Jurkat human leukemia T cells

| | % INCREASE | | | |
|---|---|---|---|---|
| | 24 h | | 48 h | |
| SEQUENCE | −CHX | +CHX | −CHX | +CHX |
| GGGTGG SEQ ID NO:5-(6 bases) 10 μg/ml | 63 | 5 | 91 | 51 |

TABLE 10-continued

Percentage increase of Fas on Jurkat human leukemia T cells

| | % INCREASE | | | |
|---|---|---|---|---|
| | 24 h | | 48 h | |
| SEQUENCE | −CHX | +CHX | −CHX | +CHX |
| GGGTGG SEQ ID NO:5-(6 bases) 100 μg/ml | 62 | 22 | 150 | 115 |

As shown in Table 10, SEQ ID NO:5 upregulated Fas expression on Jurkat T cells. With 10 μg/ml of SEQ ID NO:5, cycloheximide decreased Fas expression 92% after 24 h and 44% after 48 h. With 100 μg/ml of SEQ ID NO:5 cycloheximide decreased Fas expression 65% after 24 h and 23% after 48 h. These data suggest that 6 base SEQ ID NO:5 stimulates de novo synthesis of Fas.

EXAMPLE 13

Synergistic Effect of SEQ ID No:5 (GGGTGG) and Agonistic Anti-Fas Antibodies on Inhibition of UMUC-3 Bladder Cancer Cell Proliferation UMUC-3 bladder cancer cells were incubated for 48 hours with 0.00, 0.02 and 0.20 μg/ml of agonistic anti-Fas monoclonal antibodies (clone CH-11: Coulter-Immunotech, Marseille, France)+0 or 10 μg/ml of SEQ ID NO:5. Cell proliferation was measured using dimethylthiazol-diphenyltetrazolium (MTT) reduction (Mosman et al. J. Immunol. Methods 65:55, 1983). MTT was measured at a wavelength of 570 nm using a multiplate spectrophotometer reader (ELX800, Bio-TEK Instruments Inc., Winooski, Vt.).

TABLE 11

Inhibition of UMUC-3 bladder cancer cell proliferation

| | % INHIBITION Anti-Fas antibodies | | |
|---|---|---|---|
| SEQUENCE | 0.0 μg/ml | 0.02 μg/ml | 0.2 μg/ml |
| No sequence | 0 | 7 | 17 |
| GGGTGG SEQ ID NO:5-(6 bases) 10 μg/ml | 23 | 38 | 44 |

As shown in Table 11, 6 base SEQ ID NO:5 potentiated the inhibitory activity of 0.02 and 0.2 μg/ml of agonistic anti-Fas antibodies on UMUC-3 cell proliferation.

EXAMPLE 14

Additive Effect of SEQ ID NO:5 (GGGTGG) and Agonistic Anti-Fas Antibodies on Inhibition of Jurkat Leukemia T Cell Proliferation.

Jurkat T leukemia cells were incubated for 48 hours with 0.00, 0.02 and 0.20 μg/ml of agonistic anti-Fas monoclonal antibodies (clone CH-11)+0 and 10 μg/ml of SEQ ID NO:5. Cell proliferation was measured as in Example 13.

TABLE 12

Inhibition of Jurkat human leukemia T cell proliferation

| SEQUENCE | % INHIBITION Anti-Fas antibodies | | |
|---|---|---|---|
| | 0.0 µg/ml | 0.02 µg/ml | 0.2 µg/ml |
| No sequence | 0 | 16 | 33 |
| GGGTGG SEQ ID NO:5-(6 bases) 10 µg/ml | 16 | 28 | 48 |

As shown in Table 12, the effects of 6 base SEQ ID NO:5 and of 0.02 and 0.2 µg/ml of agonistic anti-Fas antibodies on Jurkat T cell proliferation were additive.

EXAMPLE 15

Effect of 6 Base Sequences and Agonistic Anti-Fas Antibodies on EL-4 Murine T Lymphomas EL-4 murine T lymphoma cells are implanted into C57/BL6 lpr/lpr (Fas negative mice). The mice are divided into 30 groups of 10 mice. On day 0, group 1 mice receive saline, group 2 mice receive 1, 10 or 100 mg/kg of SEQ. ID NO:5, group 3 mice receive 1, 10 or 100 mg/kg of SEQ. ID NO:16, group 4 receive 1, 10 or 100 mg/kg of SEQ. ID NO:17, group 5 mice receive 1, 10 or 100 mg/kg of SEQ. ID NO:18, group 6 mice receive anti-Fas antibodies, group 7 mice receive 1, 10 or 100 mg/kg of SEQ. ID NO:5+anti-Fas antibodies, group 8 mice receive 1, 10 or 100 mg/kg of SEQ. ID NO:16+anti-Fas antibodies, group 9 receive 1, 10 or 100 mg/kg of SEQ. ID NO:17+anti-Fas antibodies, group 10 mice receive 1, 10 or 100 mg/kg of SEQ. ID NO:18+anti-Fas antibodies. In these different groups, anti-Fas antibodies are administered at any dose in the range of about 0.003 to about 0.3 mg/kg. Group 1 mice have the most tumor mass, groups 2, 3, 4, 5 and 6 mice have less tumor mass than group 1 mice, and group 7, 8, 9 and 10 mice have the least tumor mass. The efficacy of the SEQ. ID NO:5, the SEQ. ID NO:16 and the SEQ. ID NO:17 is dose-dependent.

EXAMPLE 16

Female (SJL/J×PL/J) F1 mice are injected subcutaneously in both femoral regions with an emulsion containing 0.5 mg of myelin basic protein (MBP) mixed with complete Freund's adjuvant. After 24 h, 400 ng of *Bordetella pertussis* toxin is administered intraperitoneally. On the day of onset (day 0), group 1 mice receive saline, group 2 mice receive 1, 10 or 100 mg/kg of SEQ. ID NO:5, group 3 mice receive 1, 10 or 100 mg/kg of SEQ. ID NO:16, group 4 mice receive 1, 10 or 100 mg/kg of SEQ. ID NO:17, group 5 mice receive 1, 10 or 100 mg/kg of SEQ. ID NO: 18, group 6 mice receive anti-Fas antibodies, group 7 mice receive 1, 10 or 100 mg/kg of SEQ. ID NO:5+anti-Fas antibodies, group 8 mice receive 1, 10 or 100 mg/kg of SEQ. ID NO:16+anti-Fas antibodies, group 9 receive 1, 10 or 100 mg/kg of SEQ. ID NO:17+anti-Fas antibodies, group 10 mice receive 1, 10 or 100 mg/kg of SEQ. ID NO: 18+anti-Fas antibodies for 3 days by intracistemal administration (20 µg/day). In these different groups, anti-Fas antibodies are administered at any dose in the range of about 0.003 to about 0.3 mg/kg. Group 6, 7, 8, 9 and 10 mice show less progression of EAE than group 1, 2, 3, 4 and 5 mice. Group 7, 8, 9 and 10 mice show the least progression of EAE. The efficacy of the SEQ. ID NO:5, the SEQ. ID NO: 16 and the SEQ. ID NO:17 is dose-dependent.

We claim:

1. A method of modulating Fas or FasL expression in an animal or a human, comprising administering to the animal or the human an amount of a composition comprising a synthetic phosphodiester nucleotide and a pharmaceutically acceptable carrier, wherein the amount is effective to modulate Fas or FasL expression in the animal or the human, and the synthetic phosphodiester nucleotide is SEQ ID NO:3, SEQ ID NO:4, SEQ ID NO:6, SEQ ID NO:7, SEQ ID NO:8, SEQ ID NO:9, SEQ ID NO:10, SEQ ID NO:11, SEQ ID NO:12 or SEQ ID NO:13.

2. The method of claim 1, wherein the composition further comprises a therapeutic agent.

3. The method of claim 1, wherein the animal or the human has a disease.

4. The method of claim 3, wherein the disease is cancer.

5. The method of claim 4, wherein the cancer is ovarian cancer, prostate cancer, breast cancer, bladder cancer or leukemia.

6. The method of claim 3, wherein the disease is autoimmune encephalomyelitis.

7. The method of claim 1, wherein the animal or the human has inflammation, infection, graft rejection, tissue rejection or cell rejection.

8. The method of claim 1, wherein the effective amount is from about 0.001 to about 100 mg/kg.

9. The method of claim 8, wherein the effective amount is from about 0.01 to about 10 mg/kg.

10. The method of claim 9, wherein the effective amount is from about 0.1 to about 5 mg/kg.

11. A method of modulating efficacy of a therapeutic agent in an animal or a human comprising administering to the animal or the human an amount of a composition, comprising a synthetic phosphodiester nucleotide and a pharmaceutically acceptable carrier, wherein the amount is effective to modulate efficacy of the therapeutic agent in the animal or the human, and the synthetic phosphodiester nucleotide is SEQ ID NO:3, SEQ ID NO:4, SEQ ID NO:6, SEQ ID NO:7, SEQ ID NO:8, SEQ ID NO:9, SEQ ID NO: 10, SEQ ID NO:11, SEQ ID NO:12 or SEQ ID NO:13.

12. The method of claim 11, wherein the composition is administered before, concurrently, or after administration of the therapeutic agent.

13. The method of claim 11, wherein the animal or the human has a disease.

14. The method of claim 13, wherein the disease is cancer.

15. The method of claim 14, wherein the cancer is ovarian cancer, prostate cancer, breast cancer, bladder cancer or leukemia.

16. The method of claim 13, wherein the disease is autoimmune encephalomyelitis.

17. The method of claim 11, wherein the animal or the human has inflammation, infection, graft rejection, tissue rejection or cell rejection.

18. The method of claim 11, wherein the effective amount is from about 0.001 to about 100 mg/kg.

19. The method of claim 18, wherein the effective amount is from about 0.01 to about 10 mg/kg.

20. The method of claim 19, wherein the effective amount is from about 0.1 to about 5 mg/kg.

21. The method of claim 11, wherein the therapeutic agent is an anti-neoplastic agent, an anti-inflammatory agent, an anti-autoimmune agent, an anti-degenerative agent, a Fas modulating agent, a FasL modulating agent, radiation therapy, or a combination thereof.

22. A method of modulating Fas or FasL expression in an animal or a human having a cancer, comprising administering to the animal or the human having the cancer an amount of a composition comprising a synthetic phosphodiester nucleotide and a pharmaceutically acceptable carrier, wherein the amount is effective to modulate Fas or FasL expression in the animal or the human having the cancer, and the synthetic phosphodiester nucleotide is SEQ ID NO:1, SEQ ID NO:2, SEQ ID NO:3, SEQ ID NO:4, SEQ ID NO:6, SEQ ID NO:7, SEQ ID NO:8, SEQ ID NO:9, SEQ ID NO:10, SEQ ID NO:11, SEQ ID NO:12 or SEQ ID NO:13.

23. The method of claim 22, wherein the cancer is ovarian cancer, prostate cancer, breast cancer, bladder cancer or leukemia.

24. The method of claim 22, wherein the composition further comprises a therapeutic agent.

25. The method of claim 24, wherein the therapeutic agent is an anti-neoplastic agent, an anti-inflammatory agent, an anti-autoimmune agent, an anti-degenerative agent, a Fas modulating agent, a FasL modulating agent, radiation therapy, or a combination thereof.

26. A method of modulating efficacy of a therapeutic agent in an animal or a human having a cancer, comprising administering to the animal or the human having the cancer an amount of a composition, comprising a synthetic phosphodiester nucleotide and a pharmaceutically acceptable carrier, wherein the amount is effective to modulate efficacy of the therapeutic agent in the animal or the human having the cancer, and the synthetic phosphodiester nucleotide is SEQ ID NO:1, SEQ ID NO:2, SEQ ID NO:3, SEQ ID NO:4, SEQ ID NO:6, SEQ ID NO:7, SEQ ID NO:8, SEQ ID NO:9, SEQ ID NO:10, SEQ ID NO:11, SEQ ID NO:12 or SEQ ID NO:13.

27. The method of claim 26 wherein the cancer is ovarian cancer, prostate cancer, breast cancer, bladder cancer or leukemia.

28. The method of claim 26, wherein the composition is administered before, concurrently, or after administration of the therapeutic agent.

29. The method of claim 28, wherein the therapeutic agent is an anti-neoplastic agent, an anti-inflammatory agent, an anti-autoimmune agent, an anti-degenerative agent, a Fas modulating agent, a FasL modulating agent, radiation therapy, or a combination thereof.

* * * * *

UNITED STATES PATENT AND TRADEMARK OFFICE
CERTIFICATE OF CORRECTION

PATENT NO. : 7,662,792 B2 Page 1 of 1
APPLICATION NO. : 10/280274
DATED : February 16, 2010
INVENTOR(S) : Phillips et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1153 days.

Signed and Sealed this

Thirtieth Day of November, 2010

David J. Kappos
*Director of the United States Patent and Trademark Office*